US010105155B2

(12) United States Patent
Abri et al.

(10) Patent No.: US 10,105,155 B2
(45) Date of Patent: Oct. 23, 2018

(54) ENDOSCOPIC INSTRUMENT

(71) Applicant: Karl Storz SE & Co. KG, Tuttlingen (DE)

(72) Inventors: Omid Abri, Berlin (DE); Stephan Schrader, Kleinmachnow (DE); Jonas Forster, Berlin (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 830 days.

(21) Appl. No.: 14/460,875

(22) Filed: Aug. 15, 2014

(65) Prior Publication Data
US 2015/0051629 A1 Feb. 19, 2015

(30) Foreign Application Priority Data

Aug. 16, 2013 (DE) .................. 10 2013 013 504

(51) Int. Cl.
*A61B 17/285* (2006.01)
*A61B 17/29* (2006.01)
*A61B 17/32* (2006.01)
*A61B 17/3201* (2006.01)

(52) U.S. Cl.
CPC ............ *A61B 17/285* (2013.01); *A61B 17/29* (2013.01); *A61B 17/3201* (2013.01); *A61B 17/320016* (2013.01); *A61B 2017/2927* (2013.01)

(58) Field of Classification Search
CPC ............ A61B 17/2901; A61B 17/2909; A61B 17/2912; A61B 17/2913; A61B 17/2915; A61B 17/2916; A61B 17/2919; A61B 17/292; A61B 17/2926; A61B 17/2932; A61B 17/2933; A61B 17/2934; A61B 17/2936; A61B 17/2938; A61B 17/2939; A61B 17/30; A61B 10/06; A61B 2017/2932–2017/2941; A61B 2017/2927;
(Continued)

(56) References Cited

U.S. PATENT DOCUMENTS 6,699,235 B2 * 3/2004 Wallace .................. A61B 34/70
606/1
7,121,781 B2 10/2006 Sanchez
2003/0158576 A1 8/2003 Nagase et al.
(Continued)

FOREIGN PATENT DOCUMENTS

EP 0646356 A2 4/1995

*Primary Examiner* — Eric Rosen
*Assistant Examiner* — Mikail Mannan
(74) *Attorney, Agent, or Firm* — Whitmyer IP Group LLC

(57) ABSTRACT

An endoscopic instrument having a proximal end, a distal end, a longitudinal direction, an end effector with first and second end effector parts, a bearing element at the distal end, on which bearing element the first and second end effector parts are arranged, and first, second and third thrust elements, wherein the thrust elements each extend along the longitudinal direction and are displaceable relative to one another, wherein the first thrust element is articulately coupled to the first end effector part, the second thrust element is articulately coupled to the second end effector part, the third thrust element is articulately coupled to the first end effector part and the second end effector part, and wherein the first and second end effector parts have bearing surfaces, and the bearing surfaces are each held slidably on the bearing element.

18 Claims, 6 Drawing Sheets

(58) Field of Classification Search
CPC . A61B 17/285; A61B 17/295; A61B 17/3201;
A61B 17/320016; A61B 17/29
USPC ................................................ 606/51, 52
See application file for complete search history.

(56) References Cited

U.S. PATENT DOCUMENTS

| | | |
|---|---|---|
| 2004/0253079 A1 | 12/2004 | Sanchez |
| 2005/0187575 A1 | 8/2005 | Hallbeck et al. |
| 2007/0066986 A1 | 3/2007 | Sanchez |
| 2007/0198056 A1* | 8/2007 | Storz .................. A61B 17/2909 606/205 |
| 2008/0046000 A1 | 2/2008 | Lee et al. |
| 2008/0058861 A1 | 3/2008 | Cooper et al. |
| 2008/0255420 A1 | 10/2008 | Lee et al. |
| 2009/0209991 A1* | 8/2009 | Hinchliffe .......... A61B 17/1608 606/170 |

* cited by examiner

ENDOSCOPIC INSTRUMENT

CROSS REFERENCES TO RELATED APPLICATIONS

This application claims priority from German patent application DE 10 2013 013 504.4, filed on Aug. 16, 2013. The entire content of this priority application is incorporated herein by reference.

BACKGROUND

The present disclosure relates to an endoscopic instrument.

Conventional instruments for minimally invasive surgery (MIS) are rigid from the handle (proximal end) to the end effector (distal end), which is in particular a gripper or scissors. Here, there are normally two degrees of freedom available to the surgeon. Firstly, the shaft, and thus the end effector, can be rotated. Secondly, the end effector can be opened and closed.

Although it is possible for the surgeon to displace the endoscopic instrument laterally, this constitutes only a limited freedom of movement. Said freedom of movement becomes ever smaller the greater the depth to which a surgeon must insert the endoscopic instrument into the body of a patient, and the more sensitive the surrounding tissue is that could be damaged by a lateral displacement of the instrument.

Similar problems are also encountered by technicians who have to work with an endoscopic instrument in constricted technical spaces, for example in an engine. Both the surgeon and also the technician are restricted by the limited maneuverability and must attempt to compensate for these limitations through increased dexterity and experience.

In the prior art, various solutions have therefore been proposed for improving the mobility of the endoscopic instrument at its distal end.

U.S. Pat. No. 6,699,235 presents an endoscopic instrument which, at the distal end, can be pivoted in two mutually perpendicular planes. The apparatus is however primarily used with an end effector that does not require its own degree of freedom for its actuation, such as for example an end effector for cauterizing.

US 2008/0058861 presents an endoscopic instrument having a movable distal end on which a gripper is arranged. The construction of said instrument is however highly complex and does not provide the surgeon with direct haptic feedback as he is working.

U.S. Pat. No. 7,121,781 presents an endoscopic instrument whose distal end is arranged pivotably on a ball joint. Three pins make it possible for the distal gripper end to be displaced about two axes and for the end effector to be opened and closed. The actuation of the end effector must be performed under the control of a machine. Furthermore, there is no direct haptic feedback to the surgeon.

SUMMARY

It is an object to provide an improved endoscopic instrument which provides the surgeon with adequate freedom for the actuation of the end effector while the endoscopic instrument is in use. Here, the surgical instrument should in particular be of mechanically simple construction and permit direct haptic feedback to the surgeon. Here, the endoscopic instrument should also be as intuitive as possible to operate, such that the movements of the surgeon's hand are transmitted directly to the end effector.

According to one aspect, the object is achieved by an endoscopic instrument having:
- a proximal end,
- a distal end,
- a longitudinal direction along which the endoscopic instrument extends from the proximal end to the distal end,
- an end effector at the distal end, which end effector has a first end effector part and a second end effector part,
- a bearing element at the distal end, on which bearing element the first and second end effector parts are arranged, and on which bearing element portions of a convex surface are formed,
- a first thrust element,
- a second thrust element, and
- a third thrust element,
- wherein the thrust elements each extend along the longitudinal direction and are displaceable relative to one another along the longitudinal direction,
- wherein the first thrust element is articulately coupled to the first end effector part, the second thrust element is articulately coupled to the second end effector part, the third thrust element is articulately coupled to the first end effector part and the second end effector part, and
- wherein the first end effector part has an at least partially curved first bearing surface, and the second end effector part has an at least partially curved second bearing surface, and the first bearing surface and second bearing surface are each arranged slidably on the bearing element.

A special feature of this endoscopic instrument can be seen to lie in the fact that numerous degrees of freedom can be realized by the three thrust elements, which extend in particular into the proximal end of the endoscopic instrument, and by the end effector parts, which are arranged on the bearing element. It is accordingly possible for the first and second end effector parts, which constitute an end effector or at least one assembly of the end effector, to be displaced relative to one another, specifically in relation to the bearing element on which the first and second end effector parts are arranged.

It is furthermore possible for the two end effector parts to be displaced in the same direction and uniformly, such that the end effector can be pivoted in a first plane which is spanned by the longitudinal direction and a vertical direction. It is furthermore possible for the end effector to be pivoted in a second plane which is perpendicular to the first plane and which is spanned by the longitudinal direction and a transverse direction.

A simultaneous displacement of the first and of the second end effector parts in the first plane and in the second plane is also possible. In this way, the end effector can be pivoted in all directions; in particular, oval or circular movements of the end effector are also possible. The endoscopic instrument can furthermore be displaced along its longitudinal direction and rotated about a longitudinal axis along the longitudinal direction. The bearing surfaces lie directly, at least in some areas, on the bearing element.

It will be noted at this juncture that the expressions "longitudinal direction", "longitudinal axis" "transverse direction", "transverse axis", "vertical direction" and "vertical axis", which have been introduced above and which will appear again below, serve merely for improved orientation and ease of understanding of the structural design. The use of these expressions does not serve to establish a particular relationship with respect to some other reference system, for example the gravitational field of the Earth.

The various expressions are rather intended to highlight that certain extents of the endoscopic instrument and movements of the end effector can take place in different directions. Here, longitudinal direction and transverse direction, longitudinal direction and vertical direction, and transverse direction and vertical direction are in each case at an angle relative to one another, that is to say point in different spatial directions. Here, the endoscopic instrument can be oriented such that longitudinal direction, transverse direction and vertical direction, in each case in pairs, are at an angle of at least 45°, of at least 75° for some exemplary embodiments and of at least 85° for other exemplary embodiments with respect to one another, and may be at least approximately perpendicular to one another for yet other exemplary embodiments.

In particular, the vertical direction is to be understood as being perpendicular to the transverse direction. Since the first and second end effector parts are pivotable relative to one another, a first vertical axis of the first end effector part and a second vertical axis of the second end effector part do not have to coincide or be parallel in all positions of the end effector. Rather, during the actuation of the end effector part, in particular during an opening and closing process, an angle will be generated between the first and second vertical axes. However, the first and second vertical axes remain, except in extreme positions of the end effector part, in each case at an angle both with respect to the transverse direction and also with respect to the longitudinal direction, and, in terms of their orientation, can thus be technically distinguished from the longitudinal direction and the transverse direction.

The orientation aid that is intended to be provided by these designations will be explained once again in the figures.

The thrust elements extend in each case along the longitudinal direction, that is to say along the direction in which the endoscopic instrument extends from the proximal end to the distal end.

It will be noted that the designations "thrust element", "thrust rod" and "thrust force" are to be understood both in the sense of positive thrust and also in the sense of negative thrust, also called tension. The expressions are used merely as a linguistic simplification for an improved understanding.

The coupling between the first thrust element, the first end effector part, the second thrust element and the second end effector part may be configured in such a way that a displacement of the first thrust element and of the second thrust element towards the distal end moves the first and second end effector parts towards each other in a closing direction, and in such a way that a displacement of the first thrust element and of the second thrust element towards the proximal end moves the first and second end effector parts away from each other in an opening direction. In particular, said coupling is configured so as to be independent of a movement of the third thrust element, such that the coupling may take place without a displacement of the third thrust element, and the third thrust element is not imperatively displaced as a result of the displacement of the first and second thrust elements.

The coupling between the first thrust element, the first end effector part, the second thrust element and the second end effector part may be configured in such a way that a uniform but opposing displacement of the first thrust element and second thrust element with respect to the longitudinal direction causes a pivoting of the first and second end effector parts about the bearing element. In particular, said coupling is configured so as to be independent of a movement of the third thrust element, such that the coupling may take place without a displacement of the third thrust element, and the third thrust element is not imperatively displaced as a result of the displacement of the first and second thrust elements.

For some exemplary embodiments the coupling between the third thrust element and the first and second end effector parts may be configured in such a way that a displacement of the third thrust element with respect to the longitudinal direction causes a conjoint pivoting movement of the first and second end effector parts in each case about a first and a second vertical axis, wherein the first vertical axis and the second vertical axis are in each case perpendicular to the transverse direction. If the first and second vertical axes coincide, this may define the vertical direction along which the first and second vertical axes extend.

Moreover, a fourth thrust element may be arranged on a side of the endoscopic instrument lying opposite the side of the endoscopic instrument with the third thrust element, which fourth thrust element is moved counter to the third thrust element during a conjoint movement of the end effector part in a plane spanned by vertical direction and longitudinal direction. The fourth thrust element is articulately coupled to the first end effector part and to the second end effector part. The fourth thrust element may run parallel to the third thrust element. The explanations regarding the third thrust element and the third joint thereof apply accordingly to the fourth thrust element and to a corresponding fourth joint. The fourth thrust element permits particularly good guiding of the end effector parts. The fourth thrust element may be arranged on a second end portion of a pivot pin, on which the third thrust rod is arranged at a first end portion. The first end portion lies opposite the second end portion of the pivot pin along the longitudinal extent of the pivot pin.

In an exemplary embodiment, the first thrust element is articulately coupled to the first end effector part by a first joint, and/or the second thrust element is articulately coupled to the second end effector part by a second joint, and/or the third thrust element is articulately coupled to the first end effector part and second end effector part by means of a third joint.

This embodiment permits good transmission of the thrust or tensile force from the thrust elements to the end effector parts. Furthermore, the end effector parts can be displaced in a precise manner. All the articulated mountings to each be in the form of a joint for some exemplary embodiments. In an exemplary embodiment, a flexure hinge is used, in particular one made of spring steel or shape-memory alloys, e.g. Nitinol (nickel-titanium alloy). In another exemplary embodiment, an elastic component is used, e.g. one made of rubber or plastic.

In another exemplary embodiment, the articulated coupling of the first thrust element and the articulated coupling of the second thrust element are configured in such a way that the first end effector part and the second end effector part are pivotable relative to each other in a first pivot plane about a first pivot axis during a displacement of the first thrust element and/or of the second thrust element.

This embodiment easily permits the displacement of the first end effector part and of the second end effector part in the first pivot plane. The first and second end effector parts can be pivoted uniformly in order to obtain a pivoting of the end effector part. However, it is also possible for the first and second end effector parts to be pivoted differently in order to open or close the end effector. According to the aforementioned orientation aid, the first pivot plane lies particularly in the plane spanned by longitudinal direction and vertical direction.

In another exemplary embodiment, the articulated coupling of the third thrust element is configured in such a way that, during a displacement of the third thrust element, the first end effector part and the second end effector part are displaceable conjointly in a second pivot plane.

This embodiment easily permits displacement of the end effector in a second dimension. The articulated coupling of the third thrust element may be configured in such a way that a position of the two effector parts relative to each other remains unchanged. With regard to the aforementioned orientation aid, the second pivot plane lies in particular in the plane spanned by longitudinal direction and transverse direction. A second pivot axis, about which the end effector pivots, may extend along the vertical direction and passes in particular through the first joint and the second joint. Since the instrument can be rotated as a whole about the longitudinal direction, the end effector can therefore be opened and closed in virtually any desired position and orientation.

In another exemplary embodiment, the third thrust element is coupled to the first end effector part and the second end effector part along a first pivot axis.

The first pivot axis may be the axis about which the end effector parts can be pivoted relative to each other. Since the articulation point of the third thrust element lies along the first pivot axis, the structure is particularly simple and reliable. Since the pivot axis of the first and second end effector parts is displaced upon actuation of the third thrust element, an actuation of the third thrust element causes no force or only a slight force to be applied to the end effector parts which changes the position of the end effector parts relative to each other.

In another exemplary embodiment, the first joint is configured in such a way that the first end effector part can move relative to the first thrust element about a first rotation axis and about a further first rotation axis, wherein the first rotation axis and the further first rotation axis are at a first angle to each other, particularly at least approximately at a right angle.

This embodiment permits particularly precise control of the first end effector part during an actuation of the first thrust element and at the same time allows the displacement of the first thrust element in the second pivot plane. For some exemplary embodiments, the first joint is configured in such a way that the first end effector part can move relative to the first thrust element exclusively about the first rotation axis and about the further first rotation axis. The same considerations may also apply to the second joint in respect of the connection between the second end effector part and the second thrust element.

In another exemplary embodiment, the first pivot axis forms a longitudinal axis of a pivot pin on which the first end effector part and the second end effector part are arranged, wherein in particular the pivot pin protrudes from the bearing element at a first side and at a second side lying opposite the first side.

This embodiment is easy to implement and permits particularly precise guiding and positioning of the two end effector parts relative to each other. The connection of the end effector parts to the pivot pin can be implemented very easily if the pivot pin protrudes from the bearing element on two sides. In particular, the articulation point of the third thrust element can then also be easily formed on the pivot pin.

In another exemplary embodiment, the pivot pin is guided through a recess of the bearing element, and/or the bearing element is designed at least partially in the shape of a sphere segment.

The recess in the bearing element allows the pivot pin and the end effector parts to be easily positioned. It is possible in particular to guide the pivot pin loosely through the bearing element. In an exemplary embodiment, the pivot pin lies on the bearing element and, by tilting on a curved surface, can secure the displacement of the end effector in the second pivot plane. In another exemplary embodiment, the pivot pin is pivotably arranged on a pivot rod, which is in particular arranged centrally inside the bearing element. If the bearing element is designed at least partially in the shape of a sphere segment, the end effector parts can be displaced particularly precisely and uniformly.

In another exemplary embodiment, the first thrust element and the second thrust element lie in a first pivot plane, and the third thrust element lies in a second pivot plane perpendicular to the first pivot plane.

This embodiment easily permits displacement of the end effector in two different spatial directions, which in particular are perpendicular to each other. The first pivot plane is formed in particular by the longitudinal direction and the vertical direction. The second pivot plane is formed in particular by the longitudinal direction and the transverse direction. The second pivot plane may lie at least approximately centrally between the first thrust element and second thrust element and/or centrally between the first and second articulation point.

In another exemplary embodiment, the bearing element is stationary in relation to the proximal end, and/or the bearing element is arranged such that a displacement of one of the thrust elements always leads to a displacement of the thrust element relative to the bearing element.

The bearing element can be arranged displaceably or movably with respect to the proximal end, particularly on a holder, for example a holding tube or a holding rod. If the holder is then moved along the longitudinal direction, for example, while the first thrust element and second thrust element remain stationary, the end effector can be opened or closed. However, it is also considered for some exemplary embodiments that the bearing element is stationary relative to the proximal end. For this purpose, the bearing element is connected in particular rigidly to the proximal end of the endoscopic instrument. This technical effect is also achieved if each displacement of one of the thrust elements always leads to a displacement of this very thrust element relative to the bearing element. It is undesirable for the bearing element, if appropriate together with the holder, to execute a movement itself while one of the thrust elements is actuated. With a stationary position with respect to the proximal end, the bearing element can form a spatial reference point for the end effectors, such that it is possible to work with particularly high precision. The connection of the bearing element to the proximal end is achieved in particular by the bearing element being rigidly connected to a channel in which the thrust elements are guided, wherein the channel is connected rigidly to the proximal end.

In another exemplary embodiment, the first end effector part has a first recess and a further first recess, with which the first end effector part is held on a pivot pin.

This embodiment permits particularly precise displacement of the first end effector part. The same considerations may also apply to the second end effector part, which is then held with a second recess and a further second recess on said pivot pin.

In another exemplary embodiment, the first bearing surface has at least approximately the shape of a portion of a spherical surface, the portion resulting from a sphere being cut by two non-parallel planes which are at a plane angle to each other, the center point of the sphere lying in both planes.

This embodiment permits a particularly precise and uniform displacement of the first end effector part relative to the bearing element and also relative to the second end effector part. The same considerations may correspondingly apply to the second bearing surface. In the illustrative embodiments, a first bearing surface and a second bearing surface are shown which have at least approximately the shape of a quarter of a sphere, where said two non-parallel planes are therefore at an angle of at least approximately 90° to each other.

In another exemplary embodiment, all the thrust elements are arranged parallel to one another.

This embodiment is structurally simple and reliable. In addition, the diameter of the endoscopic instrument can thereby be kept small.

In another exemplary embodiment, the thrust elements are designed as thrust rods, in particular designed to be entirely rectilinear.

This embodiment is also structurally simple and reliable.

In another exemplary embodiment, the first end effector part is in the form of a first gripping forceps part and the second end effector part is in the form of a second gripping forceps part, or the first end effector part is in the form of a first scissor part and the second end effector part is in the form of a second scissor part.

These embodiments may make all of the required degrees of freedom available to the user in a simple manner. However, it is also possible in principle for other end effectors to be used, for example forceps, scissors, coagulation needles or fluid aspirators, and jaw parts.

It will be appreciated that the aforementioned features and the features still to be explained below can be used not only in the respectively specified combination but also in other combinations or singly, without departing from the scope and spirit of the present disclosure.

BRIEF DESCRIPTION OF THE DRAWINGS

Exemplary embodiments are depicted in the drawing and are explained in more detail in the following description. In the drawing.

DESCRIPTION OF EXEMPLARY EMBODIMENTS

Figure 1:
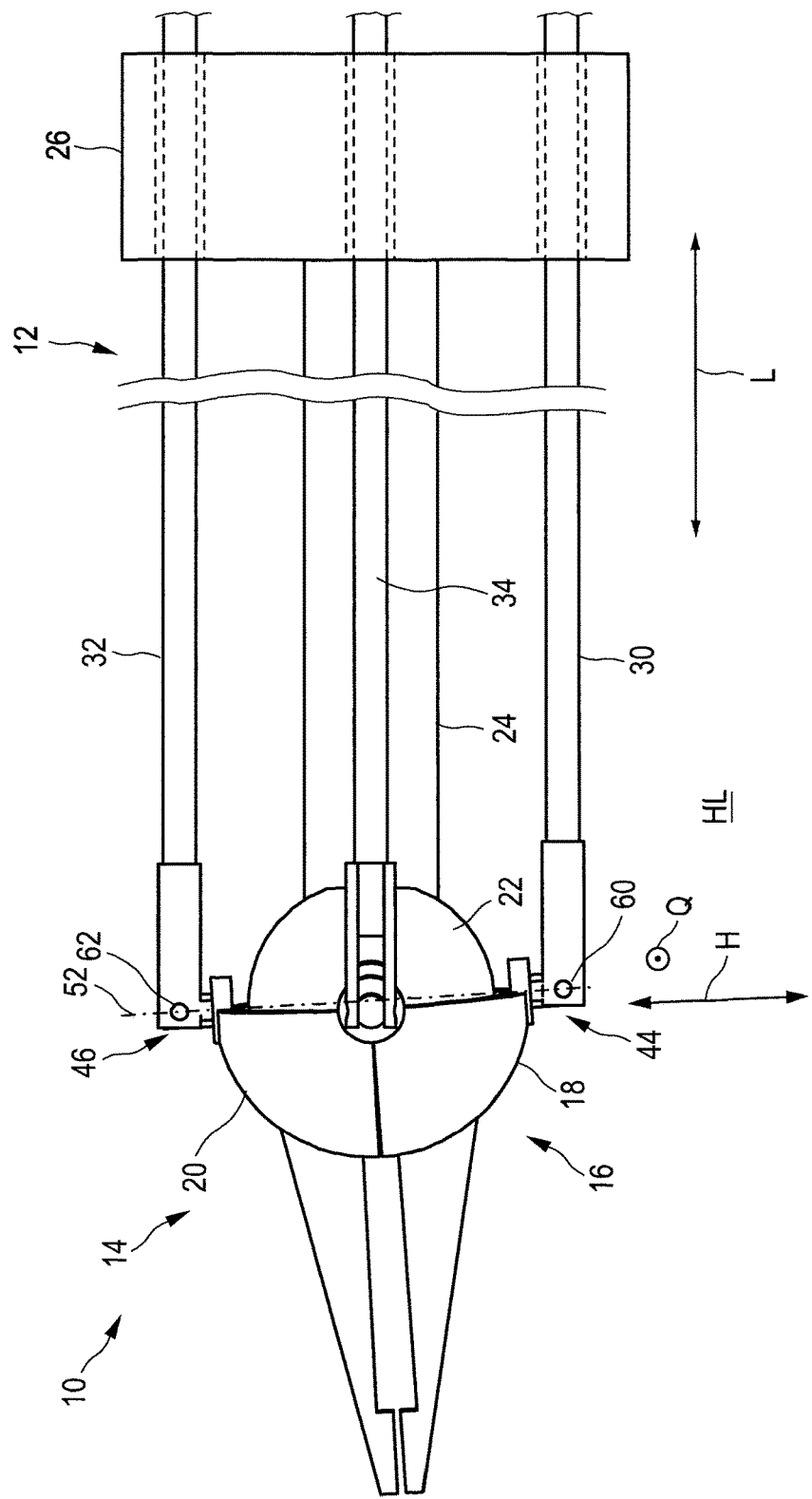
FIG. 1 shows an illustrative embodiment of an endoscopic instrument in a side view.

FIG. 1 shows a first illustrative embodiment of an endoscopic instrument 10 with a proximal end 12 and a distal end 14. A longitudinal direction L along which the endoscopic instrument 10 extends from the proximal end 12 to the distal end 14, a transverse direction Q which runs perpendicular to the longitudinal direction L, and a vertical direction H have been indicated for orientation purposes, wherein the vertical direction H runs both perpendicular to the longitudinal direction L and also perpendicular to the transverse direction Q.

At the distal end 14, the endoscopic instrument 10 has an end effector 16, which has a first end effector part 18 and a second end effector part 20. Also arranged at the distal end 14 is a bearing element 22 on which the first and second end effector parts 18, 20 are arranged. In other words, the end effector parts 18, 20 are supported on the bearing element 22 in this embodiment.

The instrument 10 has a first thrust element 30, a second thrust element 32 and a third thrust element 34. The thrust elements 30, 32, 34 extend in each case along the longitudinal direction L and are displaceable relative to one another along the longitudinal direction L.

The first thrust element 30 is articulately coupled to the first end effector part 18. The second thrust element 32 is articulately coupled to the second end effector part 20. The third thrust element 34 is articulately coupled to the first end effector part 18 and to the second end effector part 20.

The first thrust element 30 is articulately arranged on the first end effector part 18 by means of a first joint 44. Furthermore, the second thrust element 32 is also articulately arranged on the second end effector part 20 by means of a second joint 46. Although it is possible in principle for at least one of the thrust elements 30, 32 to be rigidly coupled to the respective end effector part 18, 20, both end effector parts 18, 20 can be moved individually for some exemplary embodiments. Moreover, the third thrust element 34 is also articulately arranged on the first end effector part 18 and second end effector part 20 by means of a third joint 48 (see FIG. 2).

In the embodiment shown here, the bearing element 22 is arranged on a holder 24. The holder 24 is secured on a holding block 26, wherein the holding block 26 is stationary relative to the proximal end 12. The broken lines indicate that the thrust elements 30, 32, 34 can move relative to the holding block 26 and thus relative to the holder 24 and to the bearing element 22.

The end effector 16 is pivotable in a first pivot plane HL which is spanned by the longitudinal direction L and the vertical direction H. The end effector part 16 is additionally pivotable in a second pivot plane LQ, which is spanned by the longitudinal direction L and the transverse direction Q (see FIG. 2).

The pivoting of the end effector 16 in the first pivot plane HL takes place here about a first pivot axis 50 (see FIG. 2), which here coincides with the transverse direction Q. The pivoting of the end effector 16 in the second pivot plane LQ takes place about a second pivot axis 52, which here coincides with the vertical direction H. The first thrust element 30 is coupled to the first end effector part 18 at a first articulation point 60, the second thrust element 32 is coupled to the second end effector part 20 at a second articulation point 62, and the third thrust element 34 is coupled to the first end effector part 18 and second end effector part 20 at a third articulation point 64 (see FIG. 2).

Figure 2:
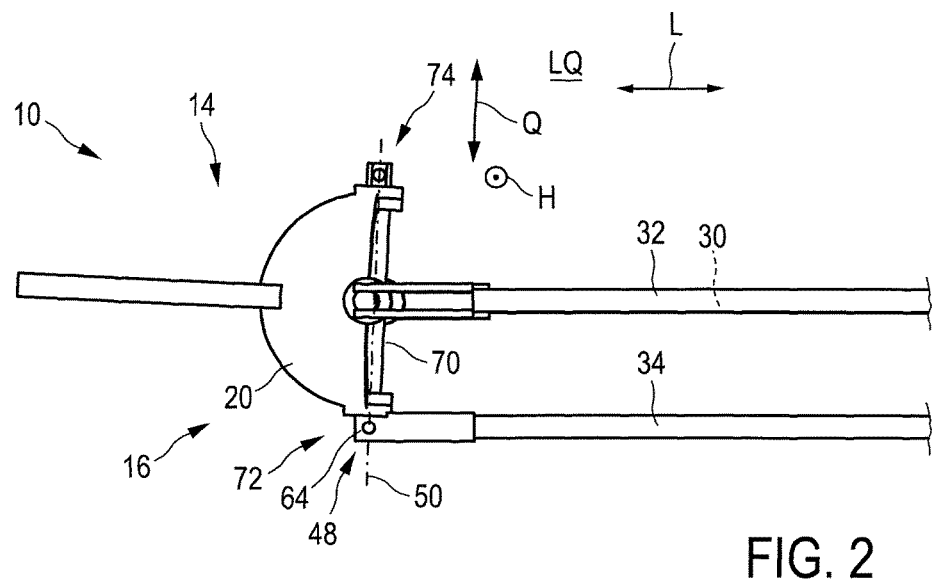
FIG. 2 shows the front part of the illustrative embodiment in a plan view, without the bearing element.

FIG. 2 shows the front part of the illustrative embodiment in a plan view. In this illustration, the proximal end 12, the bearing element 22 and the holder 24 have been omitted.

It will be seen that the pivot axis 50 forms a longitudinal axis of a pivot pin 70, on which the third thrust element 34 is articulated via the articulation point 64. Since both the first end effector part 18 and also the second end effector part 20 are arranged on the pivot pin 70, the third thrust element 34 is in this way coupled to the first end effector part 18 and second end effector part 20. It will be seen that the pivot pin 70 protrudes from the bearing element 22 both at a first side 72 and also at a second side 74 (see FIG. 1).

The first thrust element 30 and the second thrust element 32 lie in a first pivot plane HL. The third thrust element 34 lies in the second pivot plane LQ perpendicular to the first pivot plane HL.

The thrust elements 30, 32, 34 are here arranged parallel to one another. They are designed here as thrust rods, in particular designed to be entirely rectilinear. The first end effector part 18 is in the form of a first gripping forceps part, and the second end effector part 20 is in the form of a second gripping forceps part.

Figure 3:
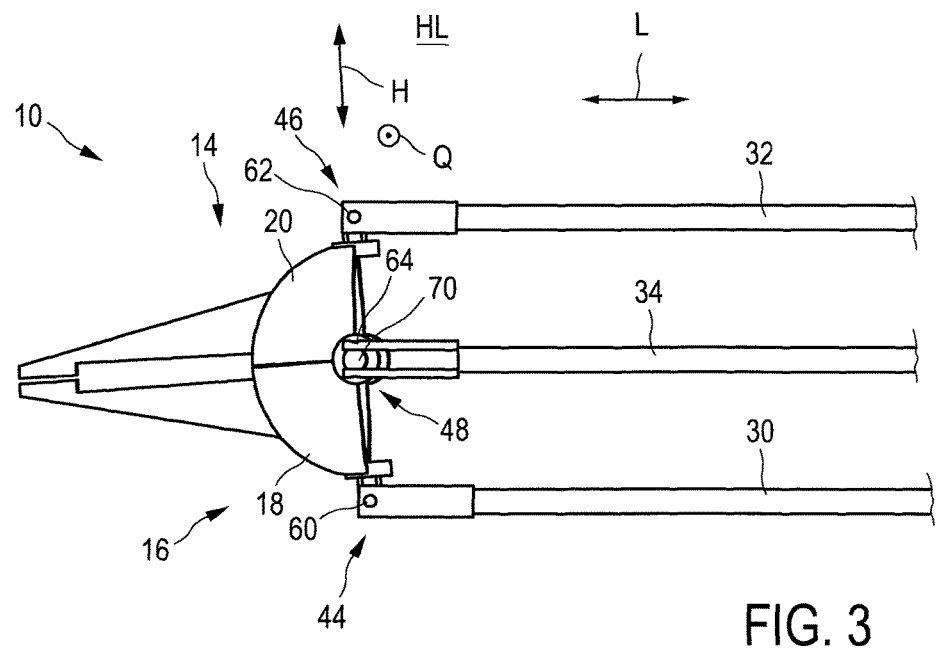
FIG. 3 shows the front part of the illustrative embodiment in the side view, without the bearing element.

FIG. 3 shows the front part of the illustrative embodiment in the side view, but here without the bearing element 22 and the holder 24, as compared to FIG. 1. The observations already made regarding FIGS. 1 and 2 apply.

Figure 4:
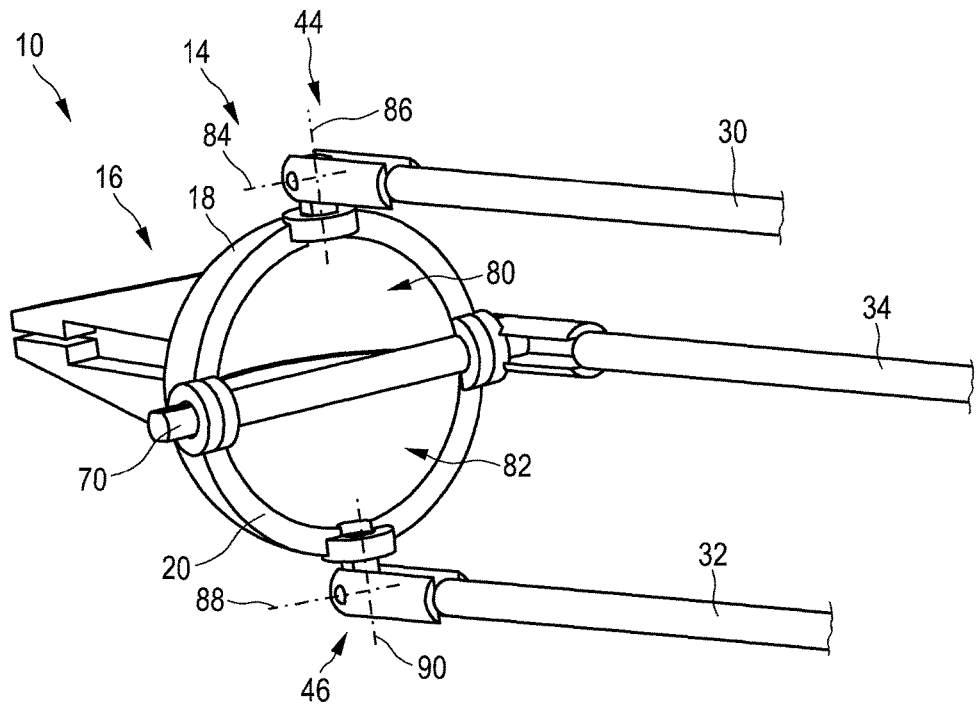
FIG. 4 shows the illustrative embodiment in a view directed to the bearing surfaces of the end effectors parts.

FIG. 4 shows the illustrative embodiment in a view directed to the bearing surfaces 80, 82 of the end effector parts 18, 20. The first bearing surface 80 and the second bearing surface 82 are at least partially curved and have here in each case approximately the shape of quarter of a sphere. The bearing surfaces 80, 82 are closed for some exemplary embodiments. However, in some embodiments, the bearing surfaces 80, 82 can also have recesses and/or projections and/or indents.

The first joint 44 is configured in such a way that the first end effector part 18 can move relative to the first thrust element 30 about a first rotation axis 84 and about a further first rotation axis 86. In particular, the first joint 44 is configured in such a way that the first end effector part 18 can move relative to the first thrust element 30 only about the first rotation axis 84 and the further first rotation axis 86.

The second joint 46 is configured in such a way that the second end effector part 20 can move relative to the second thrust element 32 about a second rotation axis 88 and about a further second rotation axis 90. In particular, the second joint 46 is configured in such a way that the second end effector part 20 can move relative to the second thrust element 32 only about the second rotation axis 88 and the further second rotation axis 90. In another exemplary embodiment, a fourth thrust element (not shown) is arranged at the free end of the pivot pin 70 (here in the foreground), which fourth thrust element is moved counter to the third thrust element 34 during a conjoint displacement of the end effector parts 18, 20 in the HL plane. The fourth thrust element may run parallel to the third thrust element 34. The connection of the fourth thrust element to the pivot pin 70 may be configured in the same way as the connection of the third thrust element 34 to the pivot pin 70.

Figure 5:
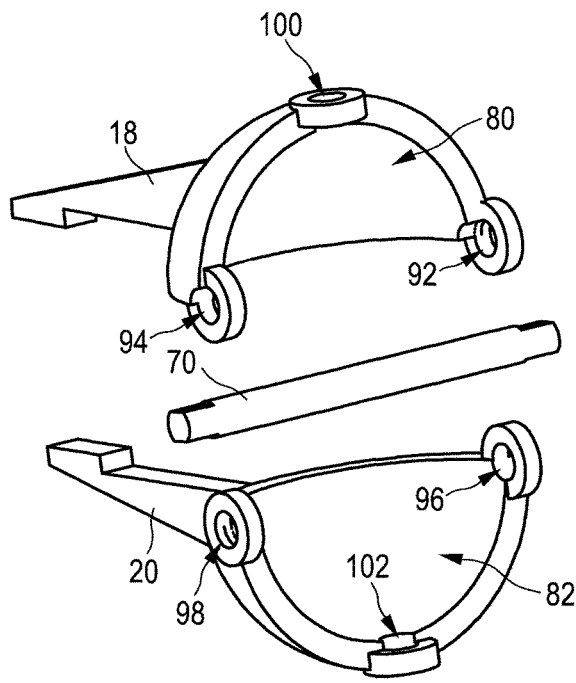
FIG. 5 shows an exploded view of the end effectors parts and of the pivot pin of the illustrative embodiment.

FIG. 5 shows an exploded view of the end effector parts 18, 20 and of the pivot pin 70. The first end effector part 18 has a first recess 92 and a further first recess 94, with which the first end effector part 18 is held on the pivot pin 70. The second end effector part 20 has a second recess 96 and a further second recess 98, with which the second end effector part 20 is held on the pivot pin 70. An additional first recess 100 and an additional second recess 102 can also be seen via which the first thrust element 30 and the second thrust element 32 are coupled to the end effector parts 18 and 20, respectively.

Figure 6:
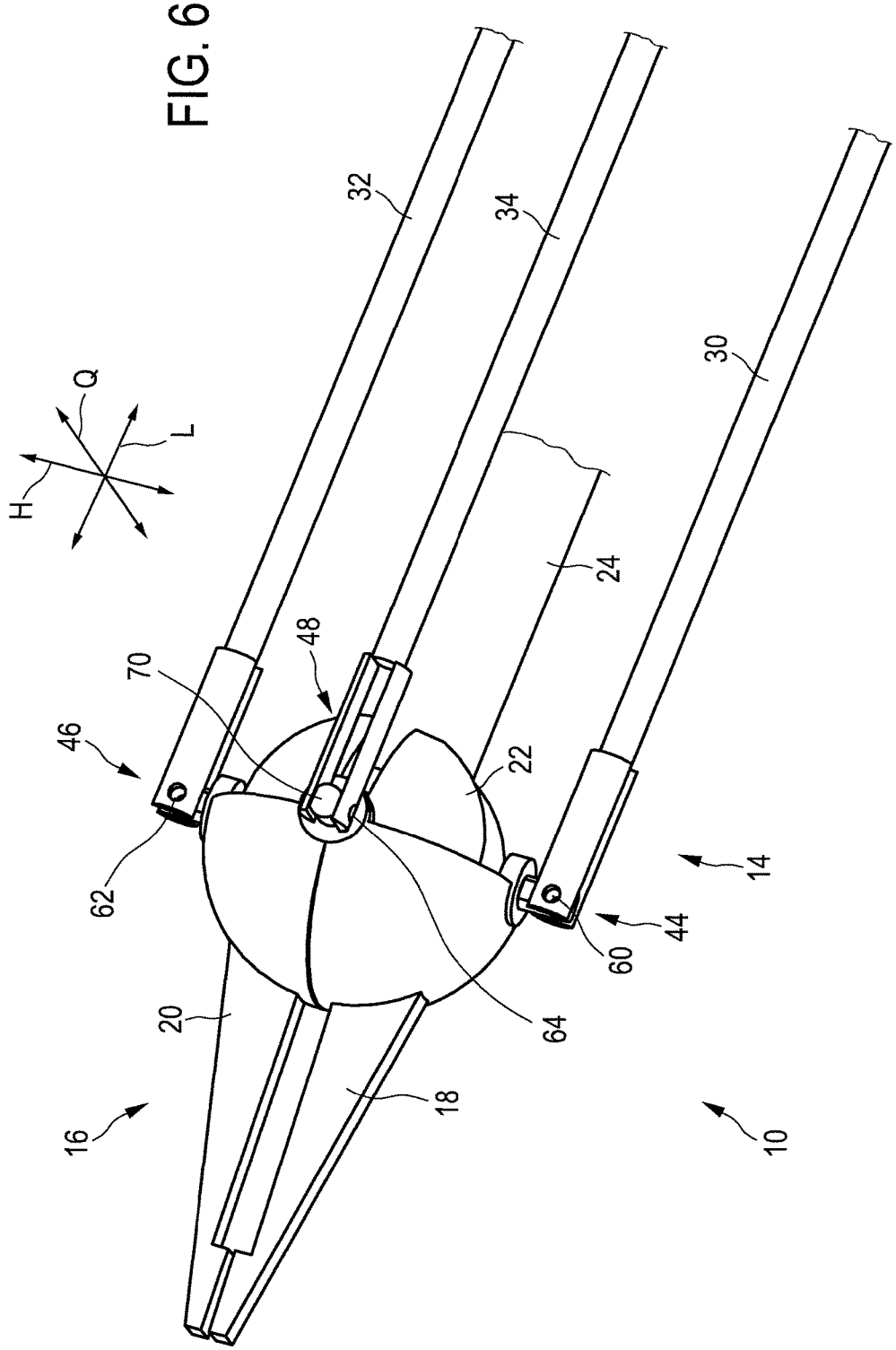
FIG. 6 shows the front part of the illustrative embodiment in a perspective view.

FIG. 6 shows the front part of the illustrative embodiment in a perspective view. All the observations made above still apply.

Figure 7:
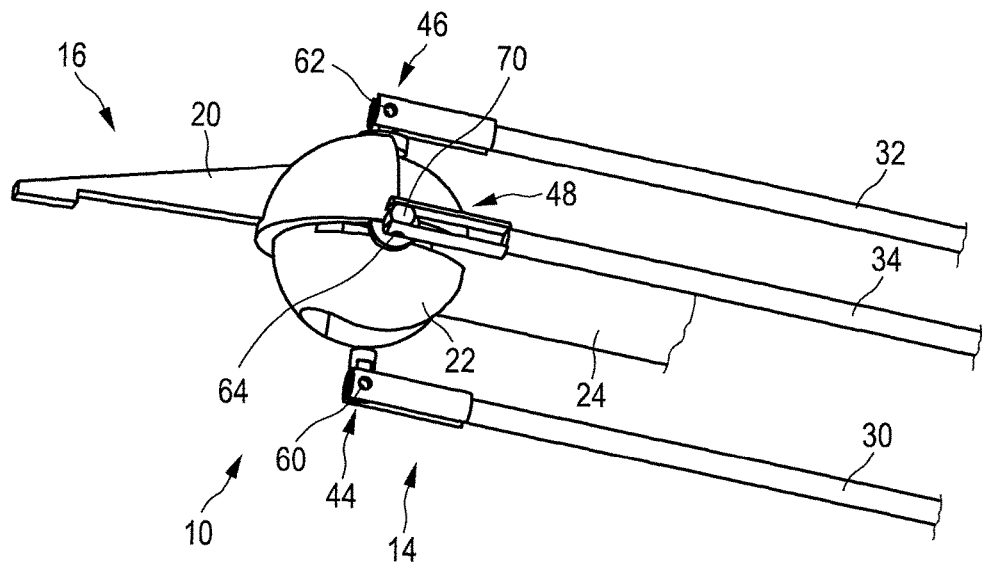
FIG. 7 shows the view as per FIG. 6, without the first end effector part.
Figure 8:
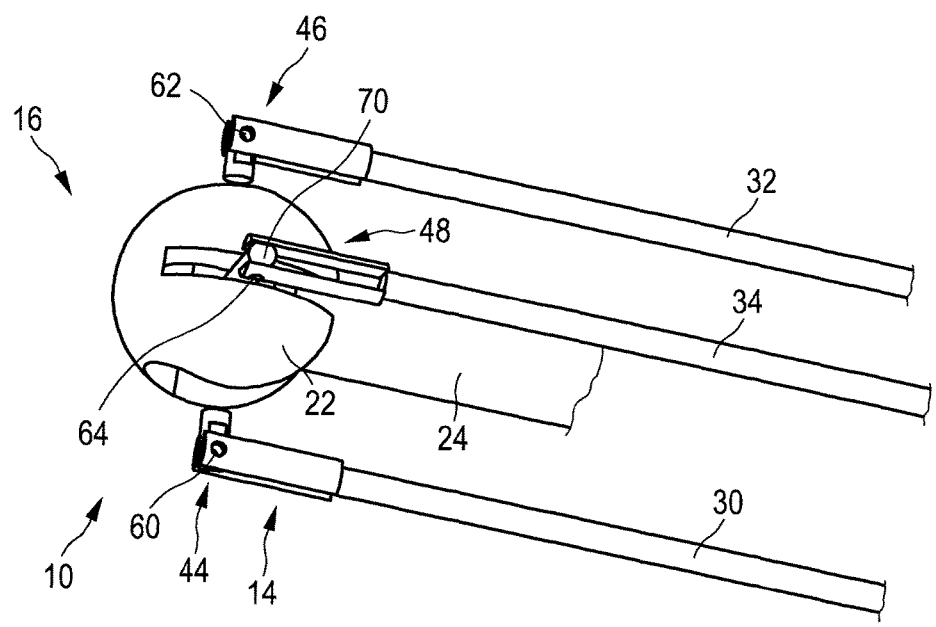
FIG. 8 shows the view as per FIG. 7, without the second end effector part.
Figure 9:
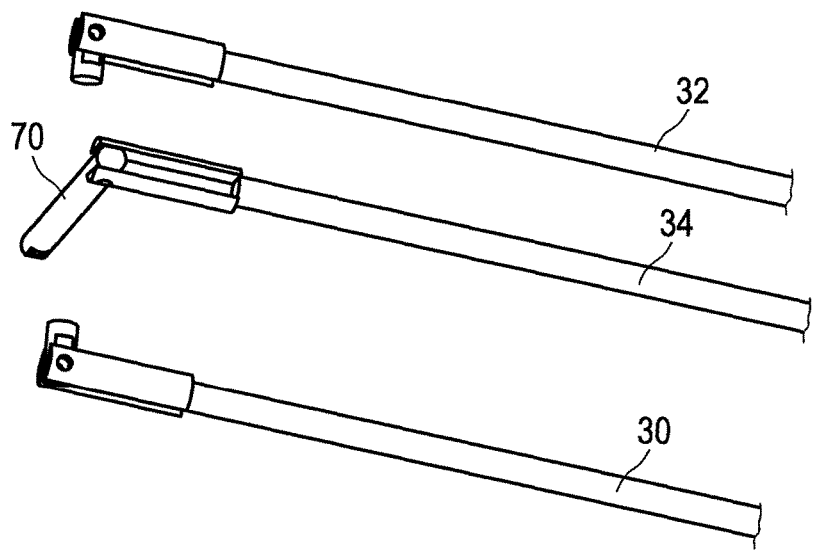
FIG. 9 shows the view as per FIG. 8, without the bearing element.

FIG. 7 shows the view as per FIG. 6, but without the first end effector part 18. This illustration permits a view of the bearing element 22. All the statements already made above still apply. FIG. 8 shows the view as per FIG. 7, but without the second end effector part 20. The bearing element 22 can now be seen even better. All the statements already made above still apply. FIG. 9 shows the view as per FIG. 8, but without the bearing element 22 and the holder 24. This shows particularly clearly the points where the end effector parts 18, 20 are coupled to the thrust elements 30, 32, 34 via the respective joints 44, 46, 48.

Figure 10:
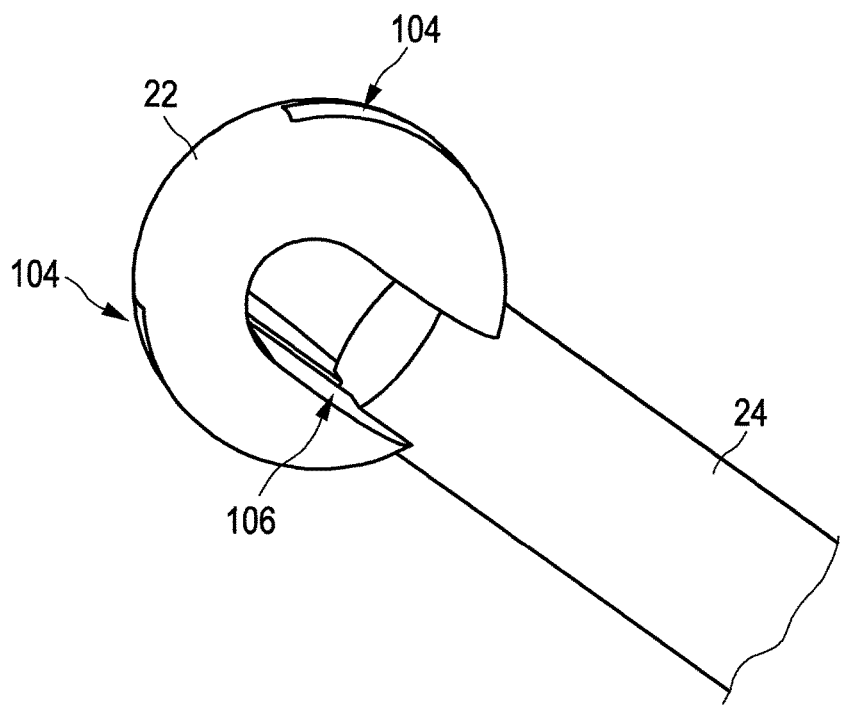
FIG. 10 shows the bearing element of the illustrative embodiment.

FIG. 10 shows the bearing element 22 with the holder 24 in a detail view. The recess 104 can be seen, through which the pivot pin 70 is guided through the bearing element 22. It will also be seen that the bearing element 22 is designed at least partially in the shape of a sphere segment. Sphere segment is to be understood as meaning that at least parts of a sphere are recognizable, but the sphere does not have to be complete, and the surface of the sphere can have recesses. The bearing element 22 also has a further recess 106.

Altogether, therefore, an endoscopic instrument 10 has been presented which, with a solution that can be realized by mechanical means, offers the surgeon numerous degrees of freedom for the actuation of the end effector and, in so doing, also permits intuitive operation.

What is claimed is:

1. An endoscopic instrument having
    a proximal end;
    a distal end;
    a longitudinal direction along which the endoscopic instrument extends from the proximal end to the distal end;
    an end effector at the distal end, wherein the end effector has a first end effector part and a second end effector part;
    a bearing element at the distal end, on which bearing element the first and second end effector parts are arranged and on which bearing element portions of a curved surface are formed;
    a first thrust element;
    a second thrust element; and
    a third thrust element;
    wherein the first, second and third thrust elements each extend along the longitudinal direction and are displaceable relative to one another along the longitudinal direction;
    wherein the first thrust element is articulately coupled to the first end effector part, the second thrust element is articulately coupled to the second end effector part, the third thrust element is articulately coupled to the first end effector part and the second end effector part;
    wherein the first end effector part has an at least partially curved first bearing surface, and the second end effector part has an at least partially curved second bearing surface, and the first and second bearing surfaces are each held slidably on the bearing element;
    wherein the first and second thrust elements are articulately coupled in such a way that the first end effector part and the second end effector part are pivotable relative to each other in a first pivot plane about a first pivot axis during a displacement of at least one of the first thrust element and the second thrust element relative to one another; and wherein the third thrust element is articulately coupled in such a way that, during a displacement of the third thrust element in the longitudinal direction and relative to at least one of the first thrust element and the second thrust element, the first end effector part and the second end effector part are displaceable in a same direction in a second pivot plane.

2. The endoscopic instrument of claim 1, wherein the first thrust element is articulately coupled to the first end effector part by a first joint.

3. The endoscopic instrument of claim 2, wherein the first joint is configured in such a way that the first end effector part can move relative to the first thrust element about a first rotation axis and about a further first rotation axis, wherein the first rotation axis and the further first rotation axis are at a first angle to each other.

4. The endoscopic instrument of claim 2, wherein the first joint is configured in such a way that the first end effector part can move relative to the first thrust element about a first rotation axis and about a further first rotation axis, wherein the first rotation axis and the further first rotation axis are at least approximately at a right angle relative to one another.

5. The endoscopic instrument of claim 1, wherein the third thrust element is coupled to the first end effector part and the second end effector part along the first pivot axis.

6. The endoscopic instrument of claim 1, wherein the first pivot axis forms a longitudinal axis of a pivot pin on which the first end effector part and the second end effector part are arranged.

7. The endoscopic instrument of claim 6, wherein the pivot pin protrudes from the bearing element at a first side and at a second side lying opposite the first side.

8. The endoscopic instrument of claim 6, wherein the pivot pin is guided through a recess of the bearing element.

9. The endoscopic instrument of claim 1, wherein the bearing element is designed at least partially in the shape of a spherical segment.

10. The endoscopic instrument of claim 1, wherein the first thrust element and the second thrust element lie in the first pivot plane, and the third thrust element lies in a second pivot plane perpendicular to the first pivot plane.

11. The endoscopic instrument of claim 1, wherein the bearing element is stationary in relation to the proximal end.

12. The endoscopic instrument of claim 1, wherein the bearing element is arranged such that a displacement of one of the first, second and third thrust elements always leads to a displacement of the displaced thrust element relative to the bearing element.

13. The endoscopic instrument of claim 1, wherein the first end effector part has a first recess and a further first recess, with which the first end effector part is held on a pivot pin.

14. The endoscopic instrument of claim 1, wherein the first bearing surface has at least approximately the shape of a portion of a spherical surface, the portion resulting from a sphere being cut by two non-parallel planes which are at an angle to each other, the center point of the sphere lying in both planes.

15. The endoscopic instrument of claim 1, wherein the first, second and third thrust elements are arranged parallel to one another.

16. The endoscopic instrument of claim 1, wherein the first, second and third thrust elements are designed as thrust rods.

17. The endoscopic instrument of claim 1, wherein the first end effector part is in the form of one of a first gripping forceps part and first scissor part, and wherein the second end effector part is in the form of one of a second gripping forceps part and a second scissor part.

18. An endoscopic instrument having
a proximal end;
a distal end;
a longitudinal direction along which the endoscopic instrument extends from the proximal end to the distal end;
an end effector at the distal end, wherein the end effector has a first end effector part and a second end effector part;
a bearing element at the distal end, on which bearing element the first and second end effector parts are arranged;
a first thrust element;
a second thrust element; and
a third thrust element;
wherein the first, second and third thrust elements each extend along the longitudinal direction;
wherein the first thrust element is articulately coupled to the first end effector part, the second thrust element is articulately coupled to the second end effector part, the third thrust element is articulately coupled to the first end effector part and the second end effector part;
wherein the first end effector part comprises a first bearing surface, and the second end effector part comprises a second bearing surface, and the first and second bearing surfaces are each held slidably on the bearing element;
wherein the first and second thrust elements are articulately coupled in such a way that the first end effector part and the second end effector part are pivotable relative to each other in a first pivot plane about a first pivot axis during a displacement of at least one of the first thrust element and the second thrust element relative to one another; and
wherein the third thrust element is articulately coupled in such a way that, during a displacement of the third thrust element in the longitudinal direction and relative to at least one of the first thrust element and the second thrust element, the first end effector part and the second end effector part are displaceable in a same direction in a second pivot plane.

* * * * *